United States Patent
Brannan (10) Patent No.: US 8,323,275 B2
(45) Date of Patent: Dec. 4, 2012

(54) LAPAROSCOPIC PORT WITH MICROWAVE RECTIFIER

(75) Inventor: Joseph D. Brannan, Erie, CO (US)

(73) Assignee: Vivant Medical, Inc., Boulder, CO (US)

( * ) Notice: Subject to any disclaimer, the term of this patent is extended or adjusted under 35 U.S.C. 154(b) by 22 days.

(21) Appl. No.: 13/104,752

(22) Filed: May 10, 2011

(65) Prior Publication Data

US 2011/0213241 A1    Sep. 1, 2011

Related U.S. Application Data

(63) Continuation-in-part of application No. 12/487,917, filed on Jun. 19, 2009.

(51) Int. Cl.
*A61B 18/04* (2006.01)
(52) U.S. Cl. .......... 606/33; 600/424; 343/703
(58) Field of Classification Search .......... 340/573.1, 340/600; 600/424, 430; 606/33; 250/336.1, 250/395; 343/703, 841
See application file for complete search history.

(56) References Cited

U.S. PATENT DOCUMENTS

| | | | |
|---|---|---|---|
| D223,367 S | 4/1972 | Kountz | |
| 4,215,275 A | 7/1980 | Wickersheim | |
| D263,020 S | 2/1982 | Rau, III | |
| D266,842 S | 11/1982 | Villers et al. | |
| 4,448,547 A | 5/1984 | Wickersheim | |
| D278,306 S | 4/1985 | McIntosh | |
| 4,560,286 A | 12/1985 | Wickersheim | |
| 4,580,557 A | 4/1986 | Hertzmann | |
| D295,893 S | 5/1988 | Sharkany et al. | |
| D295,894 S | 5/1988 | Sharkany et al. | |
| 4,753,248 A | 6/1988 | Engler et al. | |
| 4,966,583 A | 10/1990 | Debbas | |
| 5,183,463 A | 2/1993 | Debbas | |
| 5,301,682 A | 4/1994 | Debbas | |
| 5,350,391 A * | 9/1994 | Iacovelli | 606/170 |
| 5,375,596 A * | 12/1994 | Twiss et al. | 600/424 |
| D354,218 S | 1/1995 | Van de Peer | |
| 5,429,133 A * | 7/1995 | Thurston et al. | 600/436 |

(Continued)

FOREIGN PATENT DOCUMENTS

CN         1103807         6/1995

(Continued)

OTHER PUBLICATIONS

U.S. Appl. No. 08/136,098, filed Oct. 14, 1993, Roger A. Stern.

(Continued)

*Primary Examiner* — Eric M Blount (57) ABSTRACT

A radiation detector disposed on a microwave antenna assembly to receive unintended field exposure in an insufflated abdomen. The radiation detector includes a receiving antenna made up of at least two pieces of metal externally attached to the microwave antenna within the abdomen. The radiation detector is adapted to receive errant microwave energy that resonates in the abdomen. A rectifier is coupled between the two pieces of metal, where the pieces of metal are strips, rings, patches, or other geometric combinations. The rectifier is adapted to rectify at least a portion of the errant microwave energy. A filter is coupled to the rectifier and is adapted to convert the rectified microwave energy into a detection signal. An inflatable stop is located on a distal end of the microwave antenna and the inflatable stop is inflated when inserted within the abdomen. The inflated stop prevents inadvertent removal of the microwave antenna.

20 Claims, 6 Drawing Sheets

U.S. PATENT DOCUMENTS

| | | |
|---|---|---|
| 5,671,133 A | 9/1997 | Fujita et al. |
| D424,693 S | 5/2000 | Pruter |
| D424,694 S | 5/2000 | Tetzlaff et al. |
| D425,201 S | 5/2000 | Tetzlaff et al. |
| 6,061,551 A | 5/2000 | Sorrells et al. |
| 6,222,193 B1 | 4/2001 | Thurston et al. |
| D449,886 S | 10/2001 | Tetzlaff et al. |
| 6,332,089 B1 * | 12/2001 | Acker et al. .................. 600/424 |
| D457,958 S | 5/2002 | Dycus et al. |
| D457,959 S | 5/2002 | Tetzlaff et al. |
| 6,451,015 B1 | 9/2002 | Rittman, III et al. |
| 6,492,957 B2 | 12/2002 | Carillo, Jr. et al. |
| D487,039 S | 2/2004 | Webster et al. |
| D496,997 S | 10/2004 | Dycus et al. |
| D499,181 S | 11/2004 | Dycus et al. |
| 7,025,765 B2 | 4/2006 | Balbierz et al. |
| D525,361 S | 7/2006 | Hushka |
| D531,311 S | 10/2006 | Guerra et al. |
| D533,942 S | 12/2006 | Kerr et al. |
| D535,027 S | 1/2007 | James et al. |
| D541,418 S | 4/2007 | Schechter et al. |
| D541,938 S | 5/2007 | Kerr et al |
| 7,278,991 B2 | 10/2007 | Morris et al. |
| D564,662 S | 3/2008 | Moses et al. |
| D576,932 S | 9/2008 | Strehler |
| 7,422,586 B2 | 9/2008 | Morris et al. |
| 7,425,212 B1 | 9/2008 | Danek et al. |
| D594,736 S | 6/2009 | Esjunin |
| D594,737 S | 6/2009 | Kelly et al. |
| D606,203 S | 12/2009 | Husheer et al. |
| D613,412 S | 4/2010 | DeCarlo |
| 7,749,011 B2 | 7/2010 | Arts et al. |
| 7,863,984 B1 | 1/2011 | Behnke |
| 7,875,024 B2 | 1/2011 | Turovskiy et al. |
| D634,010 S | 3/2011 | DeCarlo |
| 2002/0087079 A1 | 7/2002 | Kaufman et al. |
| 2002/0120261 A1 | 8/2002 | Morris et al. |
| 2004/0006333 A1* | 1/2004 | Arnold et al. .................. 606/15 |
| 2005/0038419 A9* | 2/2005 | Arnold et al. .................. 606/15 |
| 2005/0137662 A1 | 6/2005 | Morris et al. |
| 2006/0030914 A1 | 2/2006 | Eggers et al. |
| 2007/0179496 A1 | 8/2007 | Swoyer et al. |
| 2007/0191825 A1 | 8/2007 | Cronin et al. |
| 2008/0183165 A1 | 7/2008 | Buysse et al. |
| 2009/0125020 A1* | 5/2009 | Douglass et al. ............... 606/41 |
| 2010/0321192 A1 | 12/2010 | Brannan |
| 2010/0321257 A1 | 12/2010 | Brannan |
| 2010/0331834 A1 | 12/2010 | Peterson et al. |
| 2011/0034913 A1 | 2/2011 | Brannan |
| 2011/0034917 A1 | 2/2011 | Brannan |
| 2011/0034919 A1 | 2/2011 | DeCarlo |
| 2011/0040300 A1 | 2/2011 | Brannan |
| 2011/0054458 A1 | 3/2011 | Behnke |
| 2011/0054459 A1 | 3/2011 | Peterson |
| 2011/0060325 A1 | 3/2011 | Bonn |
| 2011/0060326 A1 | 3/2011 | Smith et al. |
| 2011/0066144 A1 | 3/2011 | Bonn et al. |
| 2011/0071511 A1 | 3/2011 | Brannan et al. |
| 2011/0071581 A1 | 3/2011 | Behnke, II et al. |
| 2011/0071582 A1 | 3/2011 | Willyard et al. |
| 2011/0073594 A1 | 3/2011 | Bonn |
| 2011/0077632 A1 | 3/2011 | Rossetto |
| 2011/0077633 A1 | 3/2011 | Bonn et al. |
| 2011/0077634 A1 | 3/2011 | Brannan |
| 2011/0077635 A1 | 3/2011 | Bonn |
| 2011/0077636 A1 | 3/2011 | Brannan |
| 2011/0077637 A1 | 3/2011 | Brannan |
| 2011/0077638 A1 | 3/2011 | Brannan |
| 2011/0077639 A1 | 3/2011 | Brannan |
| 2011/0098695 A1 | 4/2011 | Brannan |
| 2011/0098696 A1 | 4/2011 | Brannan |
| 2011/0098697 A1 | 4/2011 | Brannan |

FOREIGN PATENT DOCUMENTS

| | | |
|---|---|---|
| DE | 390937 | 3/1924 |
| DE | 1099658 | 2/1961 |
| DE | 1139927 | 11/1962 |
| DE | 1149832 | 6/1963 |
| DE | 1439302 | 1/1969 |
| DE | 2439587 | 2/1975 |
| DE | 2455174 | 5/1975 |
| DE | 2407559 | 8/1975 |
| DE | 2415263 | 10/1975 |
| DE | 2429021 | 1/1976 |
| DE | 2460481 | 6/1976 |
| DE | 2602517 | 7/1976 |
| DE | 2504280 | 8/1976 |
| DE | 2627679 | 1/1977 |
| DE | 2540968 | 3/1977 |
| DE | 2820908 | 11/1978 |
| DE | 2803275 | 8/1979 |
| DE | 2823291 | 11/1979 |
| DE | 2946728 | 5/1981 |
| DE | 3143421 | 5/1982 |
| DE | 304596 | 7/1982 |
| DE | 3120102 | 12/1982 |
| DE | 3510586 | 10/1986 |
| DE | 3604823 | 8/1987 |
| DE | 8712328 | 3/1988 |
| DE | 3711511 | 6/1988 |
| DE | 3904558 | 8/1990 |
| DE | 3942998 | 7/1991 |
| DE | 4238263 | 5/1993 |
| DE | 4303882 | 8/1994 |
| DE | 4339049 | 5/1995 |
| DE | 29616210 | 1/1997 |
| DE | 19608716 | 4/1997 |
| DE | 19751106 | 5/1998 |
| DE | 19717411 | 11/1998 |
| DE | 19751108 | 5/1999 |
| DE | 19801173 | 7/1999 |
| DE | 19848540 | 5/2000 |
| DE | 10224154 | 12/2003 |
| DE | 10310765 | 9/2004 |
| DE | 10328514 | 3/2005 |
| DE | 102004022206 | 12/2005 |
| DE | 202005015147 | 3/2006 |
| EP | 0 246 350 | 11/1987 |
| EP | 0 521 264 | 1/1993 |
| EP | 0 556 705 | 8/1993 |
| EP | 0 558 429 | 9/1993 |
| EP | 0 836 868 | 4/1998 |
| EP | 0 882 955 | 12/1998 |
| EP | 1 159 926 | 5/2001 |
| EP | 0 648 515 | 4/2003 |
| FR | 179 607 | 11/1906 |
| FR | 1 275 415 | 10/1961 |
| FR | 1 347 865 | 11/1963 |
| FR | 2 235 669 | 1/1975 |
| FR | 2 276 027 | 1/1976 |
| FR | 2 313 708 | 12/1976 |
| FR | 2 502 935 | 10/1982 |
| FR | 2 517 953 | 6/1983 |
| FR | 2 573 301 | 5/1986 |
| FR | 2 862 813 | 5/2005 |
| FR | 2 864 439 | 7/2005 |
| JP | 5-5106 | 1/1993 |
| JP | 05-40112 | 2/1993 |
| JP | 06343644 | 12/1994 |
| JP | 07265328 | 10/1995 |
| JP | 08056955 | 3/1996 |
| JP | 08252263 | 10/1996 |
| JP | 09000492 | 1/1997 |
| JP | 09010223 | 1/1997 |
| JP | 11244298 | 9/1999 |
| JP | 2000342599 | 12/2000 |
| JP | 2000350732 | 12/2000 |
| JP | 2001008944 | 1/2001 |
| JP | 2001029356 | 2/2001 |
| JP | 2001128990 | 5/2001 |
| JP | 2001231870 | 8/2001 |
| JP | 2008142467 | 6/2008 |
| SU | 166452 | 11/1964 |
| SU | 401367 | 11/1974 |
| SU | 727201 | 4/1980 |

| WO | PCT/US99/10683 | 5/1999 |
| --- | --- | --- |
| WO | WO99/58065 | 11/1999 |
| WO | WO2010/035831 | 4/2010 |

OTHER PUBLICATIONS

U.S. Appl. No. 08/483,742, filed Jun. 7, 1995, Roger A. Stern.
U.S. Appl. No. 12/619,323, filed Nov. 16, 2009, Arnold V. DeCarlo.
U.S. Appl. No. 12/619,462, filed Nov. 16, 2009, Casey M. Ladtkow.
U.S. Appl. No. 12/620,289, filed Nov. 17, 2009, Joseph D. Brannan.
U.S. Appl. No. 12/642,623, filed Dec. 18, 2009, Prakash Manley.
U.S. Appl. No. 12/686,726, filed Jan. 13, 2010, Joseph D. Brannan.
U.S. Appl. No. 12/692,856, filed Jan. 25, 2010, Joseph D. Brannan.
U.S. Appl. No. 12/696,671, filed Jan. 29, 2010, Steven Kim.
U.S. Appl. No. 12/696,966, filed Jan. 29, 2010, Steven Kim.
U.S. Appl. No. 12/701,030, filed Feb. 5, 2010, Francesca Rossetto.
U.S. Appl. No. 12/708,974, filed Feb. 19, 2010, Joseph D. Brannan.
U.S. Appl. No. 12/709,014, filed Feb. 19, 2010, Joseph D. Brannan.
U.S. Appl. No. 12/712,864, filed Feb. 25, 2010, Joseph D. Brannan.
U.S. Appl. No. 12/713,429, filed Feb. 26, 2010, Anthony C. Lee.
U.S. Appl. No. 12/713,515, filed Feb. 26, 2010, Anthony C. Lee.
U.S. Appl. No. 12/713,641, filed Feb. 26, 2010, Anthony C. Lee.
U.S. Appl. No. 12/719,657, filed Mar. 8, 2010, Mani N. Prakash.
U.S. Appl. No. 12/722,034, filed Mar. 11, 2010, Casey M. Ladtkow.
U.S. Appl. No. 12/731,367, filed Mar. 25, 2010, Joseph D. Brannan.
U.S. Appl. No. 12/732,508, filed Mar. 26, 2010, Steven Kim.
U.S. Appl. No. 12/732,521, filed Mar. 26, 2010, Steven Kim.
U.S. Appl. No. 12/772,675, filed May 3, 2010, Brian Shiu.
U.S. Appl. No. 12/777,984, filed May 11, 2010, Joseph D. Brannan.
U.S. Appl. No. 12/786,671, filed May 25, 2010, Richard A. Willyard.
U.S. Appl. No. 12/787,639, filed May 26, 2010, Mani N. Prakash.
U.S. Appl. No. 12/792,904, filed Jun. 3, 2010, Ronald J. Podhajsky.
U.S. Appl. No. 12/792,932, filed Jun. 3, 2010, Ronald J. Podhajsky.
U.S. Appl. No. 12/792,947, filed Jun. 3, 2010, Ronald J. Podhajsky.
U.S. Appl. No. 12/792,970, filed Jun. 3, 2010, Ronald J. Podhajsky.
U.S. Appl. No. 12/793,037, filed Jun. 3, 2010, Ronald J. Podhajsky.
U.S. Appl. No. 12/823,211, filed Jun. 25, 2010, Mani N. Prakash.
U.S. Appl. No. 12/826,897, filed Jun. 30, 2010, Brian Shiu.
U.S. Appl. No. 12/826,902, filed Jun. 30, 2010, Brian Shiu.
U.S. Appl. No. 12/837,820, filed Jul. 16, 2010, Joseph D. Brannan.
U.S. Appl. No. 12/839,023, filed Jul. 19, 2010, Ronald J. Podhajsky.
U.S. Appl. No. 12/861,333, filed Aug. 23, 2010, Joseph D. Brannan.
U.S. Appl. No. 12/944,951, filed Nov. 12, 2010, Joseph D. Brannan.
U.S. Appl. No. 12/977,390, filed Dec. 23, 2010, Joseph D. Brannan.
U.S. Appl. No. 12/977,415, filed Dec. 23, 2010, Joseph D. Brannan.
U.S. Appl. No. 12/985,124, filed Jan. 5, 2011, Joseph D. Brannan.
U.S. Appl. No. 12/985,136, filed Jan. 5, 2011, Joseph D. Brannan.
U.S. Appl. No. 12/985,155, filed Jan. 5, 2011, Joseph D. Brannan.
U.S. Appl. No. 12/985,179, filed Jan. 5, 2011, Joseph D. Brannan.
U.S. Appl. No. 13/020,562, filed Feb. 3, 2011, Joseph D. Brannan.
U.S. Appl. No. 13/020,664, filed Feb. 3, 2011, Kenlyn S. Bonn.
U.S. Appl. No. 13/024,041, filed Feb. 9, 2011, Joseph D. Brannan.
U.S. Appl. No. 13/029,521, filed Feb. 17, 2011, Joseph D. Brannan.
U.S. Appl. No. 13/029,594, filed Feb. 17, 2011, Joseph D. Brannan.
U.S. Appl. No. 13/043,665, filed Mar. 9, 2011, Richard A. Willyard.
U.S. Appl. No. 13/043,694, filed Mar. 9, 2011, Richard A. Willyard.
U.S. Appl. No. 13/050,729, filed Mar. 17, 2011, Casey M. Ladtkow.
U.S. Appl. No. 13/083,185, filed Apr. 8, 2011, Arnold V. DeCarlo.
U.S. Appl. No. 13/083,256, filed Apr. 8, 2011, Joseph D. Brannan.
U.S. Appl. No. 13/098,199, filed Apr. 29, 2011, Roop L. Mahajan.
Alexander et al., "Magnetic Resonance Image-Directed Stereotactic Neurosurgery: Use of Image Fusion with Computerized Tomography to Enhance Spatial Accuracy" Journal Neurosurgery, 83 (1995), pp. 271-276.
Anderson et al., "A Numerical Study of Rapid Heating for High Temperature Radio Frequency Hyperthermia" International Journal of Bio-Medical Computing, 35 (1994), pp. 297-307.
Anonymous. (1999) Auto Suture MIBB Site Marker: Single Use Clip Applier, United States Surgical (Product instructions), 2 pages.
Anonymous. (2001) Disposable Chiba Biopsy Needles and Trays, Biopsy and Special Purpose Needles Cook Diagnostic and Interventional Products Catalog (products list), 4 pages.

Anonymous. (1987) Homer Mammalok™ Breast Lesion Needle/Wire Localizer, Namic® Angiographic Systems Division, Glens Falls, New York, (Hospital products price list), 4 pages.
Anonymous. (1999) MIBB Site Marker, United States Surgical (Sales brochure), 4 pages.
Anonymous. Blunt Tubes with Finished Ends. Pointed Cannula, Popper & Sons Biomedical Instrument Division, (Products Price List), one page, Jul. 19, 2000.
Anonymous. Ground Cannulae, ISPG, New Milford, CT, (Advertisement) one page, Jul. 19, 2000.
B. Levy M.D. et al., "Randomized Trial of Suture Versus Electrosurgical Bipolar Vessel Sealing in Vaginal Hysterectomy" Obstetrics & Gynecology, vol. 102, No. 1, Jul. 2003.
B. Levy M.D. et al., "Update on Hysterectomy New Technologies and Techniques" OBG Management, Feb. 2003.
B. Levy M.D., "Use of a New Vessel Ligation Device During Vaginal Hysterectomy" FIGO 2000, Washington, D.C.
B. F. Mullan et al., (May 1999) "Lung Nodules: Improved Wire for CT-Guided Localization," Radiology 211:561-565.
B. T. Heniford M.D. et al., "Initial Research and Clinical Results with an Electrothermal Bipolar Vessel Sealer" Oct. 1999.
Bergdahl et al., "Studies on Coagulation and the Development of an Automatic Computerized Bipolar Coagulator" Journal of Neurosurgery 75:1 (Jul. 1991), pp. 148-151.
Bulletin of the American Physical Society, vol. 47, No. 5, Aug. 2002, p. 41.
C. F. Gottlieb et al., "Interstitial Microwave Hyperthermia Applicators having Submillimetre Diameters", Int. J. Hyperthermia, vol. 6, No. 3, pp. 707-714, 1990.
C. H. Durney et al., "Antennas for Medical Applications", Antenna Handbook: Theory Application and Design, p. 24-40, Van Nostrand Reinhold, 1988 New York, V.T. Lo, S.W. Lee.
Carbonell et al., "Comparison of the Gyrus PlasmaKinetic Sealer and the Valleylab LigaSure™ Device in the Hemostasis of Small, Medium, and Large-Sized Arteries" Carolinas Laparoscopic and Advanced Surgery Program, Carolinas Medical Center, Charlotte, NC 2003.
Canus et al., "Initial Experience With the LigaSure™ Vessel Sealing System in Abdominal Surgery" Innovations That Work, Jun. 2002.
Chicharo et al., "A Sliding Goertzel Algorithm" Aug. 1996 DOS pp. 283-297 Signal Processing, Elsevier Science Publishers B.V. Amsterdam, NL, vol. 52, No. 3.
Chou, C.K., (1995) "Radiofrequency Hyperthermia in Cancer Therapy," Chapter 941n Biologic Effects of Nonionizing Electromagnetic Fields, CRC Press, Inc., pp. 1424-1428.
Chung et al., "Clinical Experience of Sutureless Closed Hemorrhoidectomy with LigaSure™" Diseases of the Colon & Rectum, vol. 46, No. 1, Jan. 2003.
Cosman et al., "Methods of Making Nervous System Lesions" In William RH, Rengachary SS (eds): Neurosurgery, New York: McGraw-Hill, vol. 111, (1984), pp. 2490-2499.
Cosman et al., "Radiofrequency Lesion Generation and its Effect on Tissue Impedance", Applied Neurophysiology, 51:230-242, 1988.
Cosman et al., "Theoretical Aspects of Radiofrequency Lesions in the Dorsal Root Entry Zone" Neurosurgery 15:(1984), pp. 945-950.
Crawford et al., "Use of the LigaSure™ Vessel Sealing System in Urologic Cancer Surger" Grand Rounds in Urology 1999, vol. 1, Issue 4, pp. 10-17.
Dulemba et al., "Use of a Bipolar Electrothermal Vessel Sealer in Laparoscopically Assisted Vaginal Hysterectomy" Sales/Product Literature; Jan. 2004.
E. David Crawford, "Evaluation of a New Vessel Sealing Device in Urologic Cancer Surgery" Sales/Product Literature 2000.
E. David Crawford, "Use of a Novel Vessel Sealing Technology in Management of the Dorsal Veinous Complex" Sales/Product Literature 2000.
Esterline, "Light Key Projection Keyboard" 2004 Advanced Input Systems, located at: <http://www.advanced-input.com/lightkey> last visited on Feb. 10, 2005.
Esterline Product Literature, "Light Key: Visualize a Virtual Keyboard. One With No Moving Parts", Nov. 1, 2003; 4 pages.
Geddes et al., "The Measurement of Physiologic Events by Electrical Impedance" Am. J. MI, Jan. Mar. 1964, pp. 16-27.

Goldberg et al., "Image-guided Radiofrequency Tumor Ablation: Challenges and Opportunities—Part I", (2001) J Vasc. Interv. Radiol, vol. 12, pp. 1021-1032.

Goldberg et al. (1995) "Saline-enhanced RF Ablation: Demonstration of Efficacy and Optimization of Parameters", Radiology, 197(P): 140 (Abstr).

Goldberg et al., "Tissue Ablation with Radiofrequency: Effect of Probe Size, Gauge, Duration, and Temperature on Lesion Volume" Acad Radio (1995) vol. 2, No. 5, pp. 399-404.

H. Schwarzmaier et al., "Magnetic Resonance Imaging of Microwave Induced Tissue Heating" Dept. of Laser Medicine & Dept. of Diagnostic Radiology; Heinrich-Heine-University, Duesseldorf, Germany; Dec. 8, 1994; pp. 729-731.

Heniford et al., "Initial Results with an Electrothermal Bipolar Vessel Sealer" Surgical Endoscopy (2001) 15:799-801.

Herman at al., "Laparoscopic Intestinal Resection With the LigaSure™ Vessel Sealing System: A Case Report" Innovations That Work, Feb. 2002.

Humphries Jr. et al., "Finite-Element Codes to Model Electrical Heating and Non-LInear Thermal Transport in Biological Media", Proc. ASME HTD-355, 131 (1997).

Ian D. McRury et al., The Effect of Ablation Sequence and Duration on Lesion Shape Using Rapidly Pulsed Radiofrequency Energy Through Electrodes, Feb. 2000, Springer Netherlands, vol. 4; No. 1, pp. 307-320.

Jarrett et al., "Use of the LigaSure™ Vessel Sealing System for Peri-Hilar Vessels in Laparoscopic Nephrectomy" Sales/Product Literature 2000.

Johnson et al., "Evaluation of a Bipolar Electrothermal Vessel Sealing Device in Hemorrhoidectomy" Sales/Product Literature, Jan. 2004.

Johnson, "Evaluation of the LigaSure™ Vessel Sealing System in Hemorrhoidectormy" American College of Surgeons (ACS) Clinic La Congress Poster (2000).

Johnson et al., "New Low-Profile Applicators for Local Heating of Tissues", IEEE Transactions on Biomedical Engineering, vol. BME-31, No. 1, Jan. 1984, pp. 28-37.

Johnson, "Use of the LigaSure™ Vessel Sealing System in Bloodless Hemorrhoidectomy" Innovations That Work, Mar. 2000.

Joseph G. Andriole M.D. et al., "Biopsy Needle Characteristics Assessed in the Laboratory", Radiology 148: 659-662, Sep. 1983.

Joseph Ortenberg, "LigaSure™ System Used in Laparoscopic 1st and 2nd Stage Orchiopexy" Innovations That Work, Nov. 2002.

K. Ogata, Modern Control Engineering, Prentice-Hall, Englewood Cliffs, N.J., 1970.

Kennedy et al., "High-burst-strength, feedback-controlled bipolar vessel sealing" Surgical Endoscopy (1998) 12: 876-878.

Kopans, D.B. et al., (Nov. 1985) "Spring Hookwire Breast Lesion Localizer: Use with Rigid-Compression. Mammographic Systems," Radiology 157(2):537-538.

Koyle et al., "Laparoscopic Palomo Varicocele Ligation in Children and Adolescents" Pediatric Endosurgery & Innovative Techniques, vol. 6, No. 1, 2002.

LigaSure™ Vessel Sealing System, the Seal of Confidence in General, Gynecologic, Urologic, and Laparaoscopic Surgery, Sales/Product Literature, Jan. 2004.

Livraghi et al., (1995) "Saline-enhanced RF Tissue Ablation in the Treatment of Liver Metastases", Radiology, p. 140 (Abstr).

Lyndon B. Johnson Space Center, Houston, Texas, "Compact Directional Microwave Antenna for Localized Heating," NASA Tech Briefs, Mar. 2008.

M. A. Astrahan, "A Localized Current Field Hyperthermia System for Use with 192-Iridium Interstitial Implants" Medical Physics. 9(3), May/Jun. 1982.

Magdy F. Iskander et al., "Design Optimization of Interstitial Antennas", IEEE Transactions on Biomedical Engineering, vol. 36, No. 2, Feb. 1989, pp. 238-246.

McGahan et al., (1995) "Percutaneous Ultrasound-guided Radiofrequency Electrocautery Ablation of Prostate Tissue in Dogs", Acad Radiol, vol. 2, No. 1: pp. 61-65.

McLellan et al., "Vessel Sealing for Hemostasis During Pelvic Surgery" Int'l Federation of Gynecology and Obstetrics Figo World Congress 2000, Washington, DC.

MDTECH product literature (Dec. 1999) "FlexStrand": product description, 1 page.

MDTECH product literature (Mar. 2000) I'D Wire: product description, 1 page.

Medtrex Brochure "The O.R. Pro 300" 1 page, Sep. 1998.

Michael Choti, "Abdominoperineal Resection with the LigaSure™ Vessel Sealing System and LigaSure™ Atlas 20 cm Open Instrument" Innovations That Work, Jun. 2003.

Muller et al., "Extended Left Hemicolectomy Using the LigaSure™ Vessel Sealing System" Innovations That Work. LJ, Sep. 1999.

Murakami, R. et al., (1995). "Treatment of Hepatocellular Carcinoma: Value of Percutaneous Microwave Coagulation," American Journal of Radiology (AJR) 164:1159-1164.

Ni Wei et al., "A Signal Processing Method for the Coriolis Mass Flowmeter Based on a Normalized . . . " Journal of Applied Sciences-Yingyong Kexue Xuebao, Shangha CN, vol. 23, No. 2:(Mar. 2005); pp. 160-184.

Ogden, "Goertzel Alternative to the Fourier Transform" Jun. 1993 pp. 485-487 Electronics World; Reed Business Publishing, Sutton, Surrey, BG, vol. 99, No. 9, 1687.

Olsson M.D. et al., "Radical Cystectomy in Females" Current Surgical Techniques in Urology, vol. 14, Issue 3, 2001.

Organ, L W., "Electrophysiologic Principles of Radiofrequency Lesion Making" Appl. Neurophysiol, vol. 39: pp. 69-76 (1976/77).

P.R. Stauffer et al., "Interstitial Heating Technologies", Thermoradiotheray and Thermochemotherapy (1995) vol. 1, Biology, Physiology, Physics, pp. 279-320.

Palazzo et al., "Randomized clinical trial of LigaSure™ versus open haemorrhoidectomy" British Journal of Surgery 2002,89,154-157

"Innovations in Electrosurgery" Sales/Product Literature; Dec. 31, 2000.

Paul G. Horgan, "A Novel Technique for Parenchymal Division During Hepatectomy" The American Journal of Surgery, vol. 181, No. 3, Apr. 2001, pp. 236-237.

Peterson et al., "Comparison of Healing Process Following Ligation with Sutures and Bipolar Vessel Sealing" Surgical Technology International (2001).

R. Gennari et al., (Jun. 2000) "Use of Technetium-99m-Labeled Colloid Albumin for Preoperative and Intraoperative Localization of Non palpable Breast Lesions," American College of Surgeons. 190(6):692-699.

Valleylab Brochure, "Reducing Needlestick Injuries in the Operating Room" 1 page, Mar. 2001.

Reidenbach, (1995) "First Experimental Results with Special Applicators for High-Frequency Interstitial Thermotherapy", Society Minimally Invasive Therapy, 4(Suppl 1):40 (Abstr).

Richard Wolf Medical Instruments Corp. Brochure, "Kleppinger Bipolar Forceps & Bipolar Generator" 3 pages, Jan. 1989.

Rothenberg et al., "Use of the LigaSure™ Vessel Sealing System in Minimally Invasive Surgery in Children" Int'l Pediatric Endosurgery Group (1 PEG) 2000.

Sayfan et al., "Sutureless Closed Hemorrhoidectomy: A New Technique" Annals of Surgery, vol. 234, No. 1, Jul. 2001, pp. 21-24.

Sengupta et al., "Use of a Computer-Controlled Bipolar Diathermy System in Radical Prostatectomies and Other Open Urological Surgery" ANZ Journal of Surgery (2001) 71.9 pp. 538-540.

Sigel et al., "The Mechanism of Blood Vessel Closure by High Frequency Electrocoagulation" Surgery Gynecology & Obstetrics, Oct. 1965 pp. 823-831.

Solbiati et al., (2001) "Percutaneous Radio-frequency Ablation of Hepatic Metastases from Colorectal Cancer: Long-term Results in 117 Patients", Radiology, vol. 221, pp. 159-166.

Solbiati et al. (1995) "Percutaneous US-guided RF Tissue Ablation of Liver Metastases: Long-term Follow-up", Radiology, pp. 195-203.

Strasberg et al., "Use of a Bipolar Vassel-Sealing Device for Parenchymal Transection During Liver Surgery" Journal of Gastrointestinal Surgery, vol. 6, No. 4, Jul./Aug. 2002 pp. 569-574.

Stuart W. Young, Nuclear Magnetic Resonance Imaging—Basic Principles, Raven Press, New York, 1984.

Sugita et al., "Bipolar Coagulator with Automatic Thermocontrol" J. Neurosurg., vol. 41, Dec. 1944, pp. 777-779.

Sylvain Labonte et al., "Monopole Antennas for Microwave Catheter Ablation", IEEE Trans. on Microwave Theory and Techniques, vol. 44, No. 10, pp. 1832-1840, Oct. 1995.
T. Matsukawa et al., "Percutaneous Microwave Coagulation Therapy in Liver Tumors", Acta Radiologica, vol. 38, pp. 410-415, 1997.
T. Seki et al., (1994) "Ultrasonically Guided Percutaneous Microwave Coagulation Therapy for Small Hepatocellular Carcinoma," Cancer 74(3):817.825.
Urologix, Inc.-Medical Professionals: Targis™ Technology (Date Unknown). "Overcoming the Challenge" located at: <http://www.urologix.com!medicaUtechnology.html > last visited on Apr. 27, 2001, 3 pages.
Urrutia et al., (1988). "Retractable-Barb Needle for Breast Lesion Localization: Use in 60 Cases," Radiology 169(3):845-847.
Valleylab Brochure, "Valleylab Electroshield Monitoring System" 2 pages, Nov. 1995.
ValleyLab Brochure, "Electosurgery: A Historical Overview", Innovations in Electrosurgery, 1999.
Vallfors et al., "Automatically Controlled Bipolar Electrocoagulation-'COA-COMP'" Neurosurgical Review 7:2-3 (1984) pp. 187-190.
W. Scott Helton, "LigaSure™ Vessel Sealing System: Revolutionary Hemostasis Product for General Surgery" Sales/Product Literature 1999.
Wald et al., "Accidental Burns", JAMA, Aug. 16, 1971, vol. 217, No. 7, pp. 916-921.
Walt Boyles, "Instrumentation Reference Book", 2002, Butterworth-Heinemann, pp. 262-264.
Wonnell et al., "Evaluation of Microwave and Radio Frequency Catheter Ablation in a Myocardium-Equivalent Phantom Model", IEEE Transactions on Biomedical Engineering, vol. 39, No. 10, Oct. 1992; pp. 1086-1095.
European Search Report EP 98300964.8 dated Dec. 13, 2000.
European Search Report EP 98944778 dated Nov. 7, 2000.
European Search Report EP 98958575.7 dated Oct. 29, 2002.
European Search Report EP 02786604.5 dated Feb. 10, 2010.
European Search Report EP 03721482 dated Feb. 6, 2006.
European Search Report EP 04009964 dated Jul. 28, 2004.
European Search Report EP 04013772 dated Apr. 11, 2005.
European Search Report EP 04015980 dated Nov. 3, 2004.
European Search Report EP 04015981.6 dated Oct. 25, 2004.
European Search Report EP 04027314 dated Mar. 31, 2005.
European Search Report EP 04027479 dated Mar. 17, 2005.
European Search Report EP 04027705 dated Feb. 10, 2005.
European Search Report EP 04710258 dated Oct. 15, 2004.
European Search Report EP 04752343.6 dated Jul. 31, 2007.
European Search Report EP 04778192.7 dated Jul. 1, 2009.
European Search Report EP 05002027.0 dated May 12, 2005.
European Search Report EP 05002769.7 dated Jun. 19, 2006.
European Search Report EP 05013463.4 dated Oct. 7, 2005.
European Search Report EP 05013895 dated Oct. 21, 2005.
European Search Report EP 05014156.3 dated Jan. 4, 2006.
European Search Report EP 05016399 dated Jan. 13, 2006.
European Search Report EP 05017281 dated Nov. 24, 2005.
European Search Report EP 05019130.3 dated Oct. 27, 2005.
European Search Report EP 05019882 dated Feb. 16, 2006.
European Search Report EP 05020665.5 dated Feb. 27, 2006.
European Search Report EP 05020666.3 dated Feb. 27, 2006.
European Search Report EP 05021025.1 dated Mar. 13, 2006.
European Search Report EP 05021197.8 dated Feb. 20, 2006.
European Search Report EP 05021777 dated Feb. 23, 2006.
European Search Report EP 05021779.3 dated Feb. 2, 2006.
European Search Report EP 05021780.1 dated Feb. 23, 2006.
European Search Report EP 05021935 dated Jan. 27, 2006.
European Search Report EP 05021936.9 dated Feb. 6, 2006.
European Search Report EP 05021937.7 dated Jan. 23, 2006.
European Search Report EP 05021939 dated Jan. 27, 2006.
European Search Report EP 05021944.3 dated Jan. 25, 2006.
European Search Report EP 05022350.2 dated Jan. 30, 2006.
European Search Report EP 05023017.6 dated Feb. 24, 2006.
European Search Report EP 05025423.4 dated Jan. 19, 2007.
European Search Report EP 05025424 dated Jan. 30, 2007.
European Search Report EP 05810523 dated Jan. 29, 2009.
European Search Report EP 06000708.5 dated May 15, 2006.
European Search Report EP 06002279.5 dated Mar. 30, 2006.
European Search Report EP 06005185.1 dated May 10, 2006.
European Search Report EP 06005540 dated Sep. 24, 2007.
European Search Report EP 06006717.0 dated Aug. 11, 2006.
European Search Report EP 06006961 dated Oct. 22, 2007.
European Search Report EP 06006963 dated Aug. 4, 2006.
European Search Report EP 06008779.8 dated Jul. 13, 2006.
European Search Report EP 06009435 dated Jul. 13, 2006.
European Search Report EP 06010499.9 dated Jan. 29, 2008.
European Search Report EP 06014461.5 dated Oct. 31, 2006.
European Search Report EP 06018206.0 dated Oct. 20, 2006.
European Search Report EP 06019768 dated Jan. 17, 2007.
European Search Report EP 06020574.7 dated Oct. 2, 2007.
European Search Report EP 06020583.8 dated Feb. 7, 2007.
European Search Report EP 06020584.6 dated Feb. 1, 2007.
European Search Report EP 06020756.0 dated Feb. 16, 2007.
European Search Report EP 06022028.2 dated Feb. 13, 2007.
European Search Report EP 06023756.7 dated Feb. 21, 2008.
European Search Report EP 06024122.1 dated Apr. 16, 2007.
European Search Report EP 06024123.9 dated Mar. 6, 2007.
European Search Report EP 06025700.3 dated Apr. 12, 2007.
European Search Report EP 07000885.9 dated May 15, 2007.
European Search Report EP 07001480.8 dated Apr. 19, 2007.
European Search Report EP 07001481.6 dated May 2, 2007.
European Search Report EP 07001485.7 dated May 23, 2007.
European Search Report EP 07001488.1 dated Jun. 5, 2007.
European Search Report EP 07001489.9 dated Dec. 20, 2007.
European Search Report EP 07001491 dated Jun. 6, 2007.
European Search Report EP 07001527.6 dated May 18, 2007.
European Search Report EP 07007783.9 dated Aug. 14, 2007.
European Search Report EP 07008207.8 dated Sep. 13, 2007.
European Search Report EP 07009026.1 dated Oct. 8, 2007.
European Search Report EP 07009028 dated Jul. 16, 2007.
European Search Report EP 07009029.5 dated Jul. 20, 2007.
European Search Report EP 07009321.6 dated Aug. 28, 2007.
European Search Report EP 07009322.4 dated Jan. 14, 2008.
European Search Report EP 07010672.9 dated Oct. 16, 2007.
European Search Report EP 07010673.7 dated Oct. 5, 2007.
European Search Report EP 07013779.9 dated Oct. 26, 2007.
European Search Report EP 07015191.5 dated Jan. 23, 2008.
European Search Report EP 07015601.3 dated Jan. 4, 2008.
European Search Report EP 07015602.1 dated Dec. 20, 2007.
European Search Report EP 07018375.1 dated Jan. 8, 2008.
European Search Report EP 07018821 dated Jan. 14, 2008.
European Search Report EP 07019173.9 dated Feb. 12, 2008.
European Search Report EP 07019174.7 dated Jan. 29, 2008.
European Search Report EP 07019178.8 dated Feb. 12, 2008.
European Search Report EP 07020283.3 dated Feb. 5, 2008.
European Search Report EP 07253835.8 dated Dec. 20, 2007.
European Search Report EP 08001019 dated Sep. 23, 2008.
European Search Report EP 08004974.5 dated Apr. 6, 2011.
European Search Report EP 08004975 dated Jul. 24, 2008.
European Search Report EP 08006731.7 dated Jul. 29, 2008.
European Search Report EP 08006733 dated Jul. 7, 2008.
European Search Report EP 08006734.1 dated Aug. 18, 2008.
European Search Report EP 08006735.8 dated Jan. 8, 2009.
European Search Report EP 08007924.7 partial dated Aug. 17, 2010.
European Search Report EP 08011282 dated Aug. 14, 2009.
European Search Report EP 08011705 dated Aug. 20, 2009.
European Search Report EP 08011705.4 extended dated Nov. 4, 2009.
European Search Report EP 08012829.1 dated Oct. 29, 2008.
European Search Report EP 08015842 dated Dec. 5, 2008.
European Search Report EP 08019920.1 dated Mar. 27, 2009.
European Search Report EP 08020530.5 dated May 27, 2009.
European Search Report EP 08169973.8 dated Apr. 6, 2009.
European Search Report EP 09010873.9 extended dated Nov. 13, 2009.
European Search Report EP 09010877.0 extended dated Dec. 3, 2009.
European Search Report EP 09012389.4 dated Jul. 6, 2010.
European Search Report EP 09151621 dated Jun. 18, 2009.

European Search Report EP 09156861.8 dated Aug. 4, 2009.
European Search Report EP 09161502.1 dated Sep. 2, 2009.
European Search Report EP 09161502.1 extended dated Oct. 30, 2009.
European Search Report EP 09165976.3 extended dated Mar. 17, 2010.
European Search Report EP 09166708 dated Oct. 15, 2009.
European Search Report EP 09166708.9 dated Mar. 18, 2010.
European Search Report EP 09169376.2 extended dated Dec. 16, 2009.
European Search Report EP 09172188.6 extended dated Apr. 23, 2010.
European Search Report EP 09172838.6 extended dated Jan. 20, 2010.
European Search Report EP 09173268.5 extended dated Jan. 27, 2010.
European Search Report EP 10001767.2 extended dated Jun. 18, 2010.
European Search Report EP 10004950.1 extended dated Jul. 2, 2010.
European Search Report EP 10004951.9 extended dated Jul. 2, 2010.
European Search Report EP 10005533.4 extended dated Sep. 24, 2010.
European Search Report EP 10005534.2 extended dated Sep. 17, 2010.
European Search Report EP 10006373.4 extended dated Nov. 11, 2010.
European Search Report EP 10008139.7 extended dated Nov. 30, 2010.
European Search Report EP 10008140.5 extended dated Dec. 28, 2010.
European Search Report EP 10008850.9 extended dated Nov. 30, 2010.
European Search Report EP 10009731.0 extended dated Jan. 28, 2011.
European Search Report EP 10009732.8 extended dated Jan. 26, 2011.
European Search Report EP 10010943.8 extended dated Feb. 1, 2011.
European Search Report EP 10011750.6 extended dated Feb. 1, 2011.
European Search Report EP 10014042.5 extended dated Feb. 18, 2011.
European Search Report EP 10158944.8 extended dated Jun. 21, 2010.
European Search Report EP 10161722.3 extended dated Jun. 16, 2010.
European Search Report EP 10163235.4 dated Aug. 10, 2010.
European Search Report EP 10185413.1 dated Dec. 7, 2010.
European Search Report EP 10185413.1 dated Mar. 14, 2011.
European Search Report EP 10191321.8 dated Apr. 7, 2011.
International Search Report PCT/US97/05066 dated Jun. 24, 1997.
International Search Report PCT/US98/18640 dated Jan. 29, 1999.
International Search Report PCT/US98/23950 dated Jan. 14, 1999.
International Search Report PCT/US99/24869 dated Feb. 11, 2000.
International Search Report PCT/US01/11218 dated Aug. 14, 2001.
International Search Report PCT/US01/11224 dated Nov. 13, 2001.
International Search Report PCT/US01/11340 dated Aug. 16, 2001.
International Search Report PCT/US01/11420 dated Oct. 16, 2001.
International Search Report PCT/US02/01890 dated Jul. 25, 2002.
International Search Report PCT/US02/11100 dated Jul. 16, 2002.
International Search Report PCT/US03/09483 dated Aug. 13, 2003.
International Search Report PCT/US03/22900 dated Dec. 2, 2003.
International Search Report PCT/US03/37110 dated Jul. 25, 2005.
International Search Report PCT/US03/37111 dated Jul. 28, 2004.
International Search Report PCT/US03/37310 dated Aug. 13, 2004.
International Search Report PCT/US04/04685 dated Aug. 27, 2004.
International Search Report PCT/US04/13273 dated Dec. 15, 2004.
International Search Report PCT/US04/15311 dated Jan. 12, 2005.
International Search Report PCT/US05/36168 dated Aug. 28, 2006.
International Search Report PCT/US08/052460 dated Apr. 24, 2008.
International Search Report PCT/US09/31658 dated Mar. 11, 2009.
International Search Report PCT/US10/032796 dated Jul. 28, 2010.

* cited by examiner

LAPAROSCOPIC PORT WITH MICROWAVE RECTIFIER

CROSS-REFERENCE TO RELATED APPLICATION

The present application is a continuation-in-part of a U.S. application Ser. No. 12/487,917 entitled "Microwave Ablation Antenna Radiation Detector" filed on Jun. 19, 2009, which is hereby incorporated by reference in its entirety.

BACKGROUND

1. Technical Field

The present disclosure relates generally to microwave antennas. More particularly, the present disclosure is directed to radiation detectors for microwave ablation antennas.

2. Background of Related Art

Treatment of certain diseases requires destruction of malignant tissue growths (e.g., tumors). It is known that tumor cells denature at elevated temperatures that are slightly lower than temperatures injurious to surrounding healthy cells. Therefore, known treatment methods, such as hyperthermia therapy, heat tumor cells to temperatures above 41° C., while maintaining adjacent healthy cells at lower temperatures to avoid irreversible cell damage. Such methods involve applying electromagnetic radiation to heat tissue and include ablation and coagulation of tissue. In particular, microwave energy is used to coagulate and/or ablate tissue to denature or kill the cancerous cells.

Microwave energy is applied via microwave ablation antennas that penetrate tissue to reach tumors. There are several types of microwave antennas, such as monopole and dipole, in which microwave energy radiates perpendicularly from the axis of the conductor. A monopole antenna includes a single, elongated microwave conductor whereas a dipole antenna includes two conductors. In a dipole antenna, the conductors may be in a coaxial configuration including an inner conductor and an outer conductor separated by a dielectric portion. More specifically, dipole microwave antennas may have a long, thin inner conductor that extends along a longitudinal axis of the antenna and is surrounded by an outer conductor. In certain variations, a portion or portions of the outer conductor may be selectively removed to provide more effective outward radiation of energy. This type of microwave antenna construction is typically referred to as a "leaky waveguide" or "leaky coaxial" antenna.

During microwave ablation, unintended field exposure to healthy tissue may occur due to incorrect device use. For example, damage to healthy tissue may occur if a surgeon inserts the probe to an insufficient depth while performing an ablation, the probe slipping out due to surgeon error or fatigue, or activation of the probe prior to placing the probe in tissue. Also, the repercussions of the unintended field exposure may increase during laparoscopic procedures due to high field intensities as a result of an insufflated abdomen acting as a resonant microwave cavity. Burns to the abdominal wall along device/probe insertion tracks have occurred due to these factors.

SUMMARY

A radiation detector disposed on a microwave antenna assembly to receive unintended field exposure in an insufflated abdomen. The radiation detector includes a receiving antenna made up of at least two pieces of metal externally attached to the microwave antenna on the distal end so as to be within the abdomen. The radiation detector is adapted to receive errant microwave energy that resonates in the abdomen. A rectifier is coupled between the two pieces of metal, where the pieces of metal are strips, rings, patches, or other geometric combinations. The rectifier is adapted to rectify at least a portion of the errant microwave energy. A filter is coupled to the rectifier and is adapted to convert the rectified microwave energy into a detection signal. An inflatable stop is located on a distal end of the microwave antenna and the stop is inflated when inserted within the abdomen. The inflated stop prevents inadvertent removal of the microwave antenna.

According to one aspect of the disclosure, a radiation detector disposed on a microwave antenna assembly is disclosed. The radiation detector includes a receiving antenna adapted to receive microwave energy. The receiving antenna is formed from two pieces of metal externally attached to a microwave antenna of the microwave antenna assembly. The radiation detector further includes at least one rectifier coupled between the pieces of metal adapted to rectify at least a portion of the microwave energy and a filter coupled to the at least one rectifier and adapted to convert the rectified microwave energy into a detection signal.

According to another aspect of the present disclosure, a microwave antenna assembly is disclosed. The microwave antenna assembly includes a hub adapted to couple the microwave antenna assembly to a microwave generator and a radiating section coupled to the hub through a feedline. The microwave antenna assembly further includes an inflatable stop surrounding the feedline. The inflatable stop is inflated when the feedline is placed within an abdomen of a patient to prevent the radiating section from inadvertently withdrawing from the abdomen. Additionally, the microwave antenna assembly includes a radiation detector disposed on the microwave antenna assembly near the radiating section. The radiation detector includes a receiving antenna adapted to receive microwave energy. The receiving antenna is formed from two pieces of metal externally attached to the feedline within the abdomen. The receiving antenna further includes at least one rectifier coupled between the pieces of metal adapted to rectify at least a portion of the microwave energy that resonates in the abdomen. Additionally, the receiving antenna includes a filter coupled to the at least one rectifier and adapted to convert the rectified microwave energy into a detection signal.

A method for detecting errant microwave energy is also contemplated by the present disclosure. The method includes the steps of receiving resonant microwave energy from an insulfated abdomen with a receiving antenna and rectifying at least a portion of the microwave energy through at least one rectifier coupled to the receiving antenna. Further the method includes the step of filtering the rectified microwave energy through a filter coupled to the at least one rectifier to convert the rectified microwave energy into a detection signal.

BRIEF DESCRIPTION OF THE DRAWINGS

The above and other aspects, features, and advantages of the present disclosure will become more apparent in light of the following detailed description when taken in conjunction with the accompanying drawings in which.

DETAILED DESCRIPTION

Particular embodiments of the present disclosure as described herein below with reference to the accompanying drawings. In the following description, well-known functions or constructions are not described in detail to avoid obscuring the present disclosure in unnecessary detail.

The present disclosure provides for a radiation detector disposed on a microwave antenna. Generally, the detector is disposed in a location such that any unintended and/or errant radiation of microwave energy within the abdomen is detected. The radiation detector converts the detected radiation into a detection signal, which is then transmitted to a control system (e.g., microwave generator) to either shut off the power supply and/or alert the user.

Figure 1:
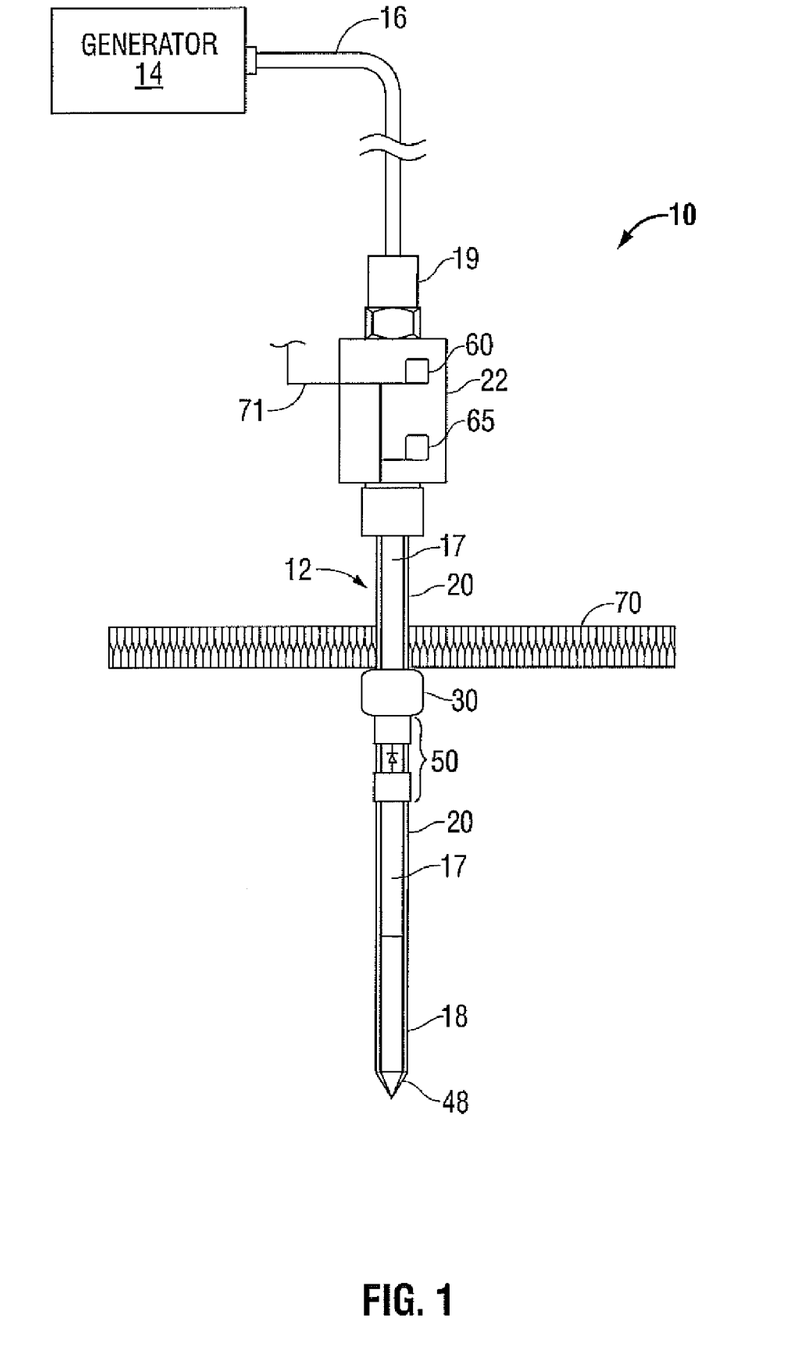
FIG. 1 is a schematic diagram of a microwave ablation system according to an embodiment of the present disclosure.

FIG. 1 shows a microwave ablation system 10 that includes a microwave antenna assembly 12 coupled to a microwave generator 14 via a flexible coaxial cable 16. The generator 14 is configured to provide microwave energy at an operational frequency from about 500 MHz to about 10,000 MHz. In the illustrated embodiment, the antenna assembly 12 includes a radiating section 18 connected by feedline 20 (or shaft) to the cable 16. More specifically, the feedline 20 is connected to a hub 22, which is connected to the cable 16 through a cable connector 19. The hub 22 may have a variety of suitable shapes, e.g., cylindrical, rectangular, etc. Further, the antenna assembly 12 includes a radiating section 18 with a tip 48 on the distal end of the feedline 20.

The feedline 20 may be coaxial and include an inner conductor surrounded by an inner insulator, which is, in turn, surrounded by an outer conductor 17 (e.g., a cylindrical conducting sheath). The inner conductor and outer conductor 17 may be constructed of copper, gold, stainless steel or other conductive metals with similar conductivity values. The metals may be plated with other materials, e.g., other conductive materials, to improve their properties, e.g., to improve conductivity or decrease energy loss, etc. In one embodiment, the feedline 20 may be formed from a coaxial, semi-rigid or flexible cable having a wire with a 0.047" outer diameter rated for 50 Ohms.

The antenna assembly 12 includes a radiation detector 50 disposed along the feedline 20 just on the inside of the abdominal wall 70. Further, the radiation detector 50 may be located near an inflatable stop 30. The radiation detector 50 is shown in detail in FIGS. 2A-2C. The radiation detector 50 is connected through a filter (See FIG. 2A) to wire 71. The wire 71 may be disposed anywhere along the antenna assembly 12 such that the wire 71 has minimal effect on the radiation efficiency of the antenna assembly 12. The wire 71 may be connected to a light emitting diode (LED) 60, a speaker 65, and/or a controller (not shown) within the generator 14.

The inflatable stop 30 is a balloon or other inflatable material that surrounds the feedline 20. The stop 30 may be formed from materials having suitable mechanical properties (such as puncture resistance, pin hole resistance, tensile strength, conformability when inflated), chemical properties (such as forming a suitable bond to the feedline 20), and biocompatibility. In another embodiment, the walls of the inflatable stop 30 may be formed from a suitable polyvinyl chloride (PVC). Other suitable materials include polypropylene, polyethylene teraphthalate (PETP), low-density polyethylene (LDPE), silicone, neoprene, polyisoprene, or polyurethane (PU).

The inflatable stop 30 is located on the distal end of the feedline 20 so as to be inside the abdomen wall 70 or body cavity wall. The location of the inflatable stop 30 may be adjusted based on the size of the abdomen and/or the depth necessary to perform the surgery.

Prior to inserting the radiating section 18 and feedline 20 within the patient's abdomen or body cavity, the inflatable stop 30 is in a collapsed form. After inserting the radiating section 18 and feedline 20 within the patient's abdomen, the inflatable stop 30 is inflated using a conduit or catheter (not shown). The inflatable stop 30 may be filled with gaseous or fluid inflation media, e.g., air, water, saline etc., in a selective manner such that inflation media may be introduced and/or withdrawn from inflatable stop 30 as desired. Once inflated, the inflatable stop 30 prevents inadvertent removal of the radiating section 18. Inadvertent removal may cause ablation to the wrong tissue. The inflatable stop 30 is then deflated upon completion of the procedure to allow removal of the radiating section 18 and feedline 20.

Figure 2A:
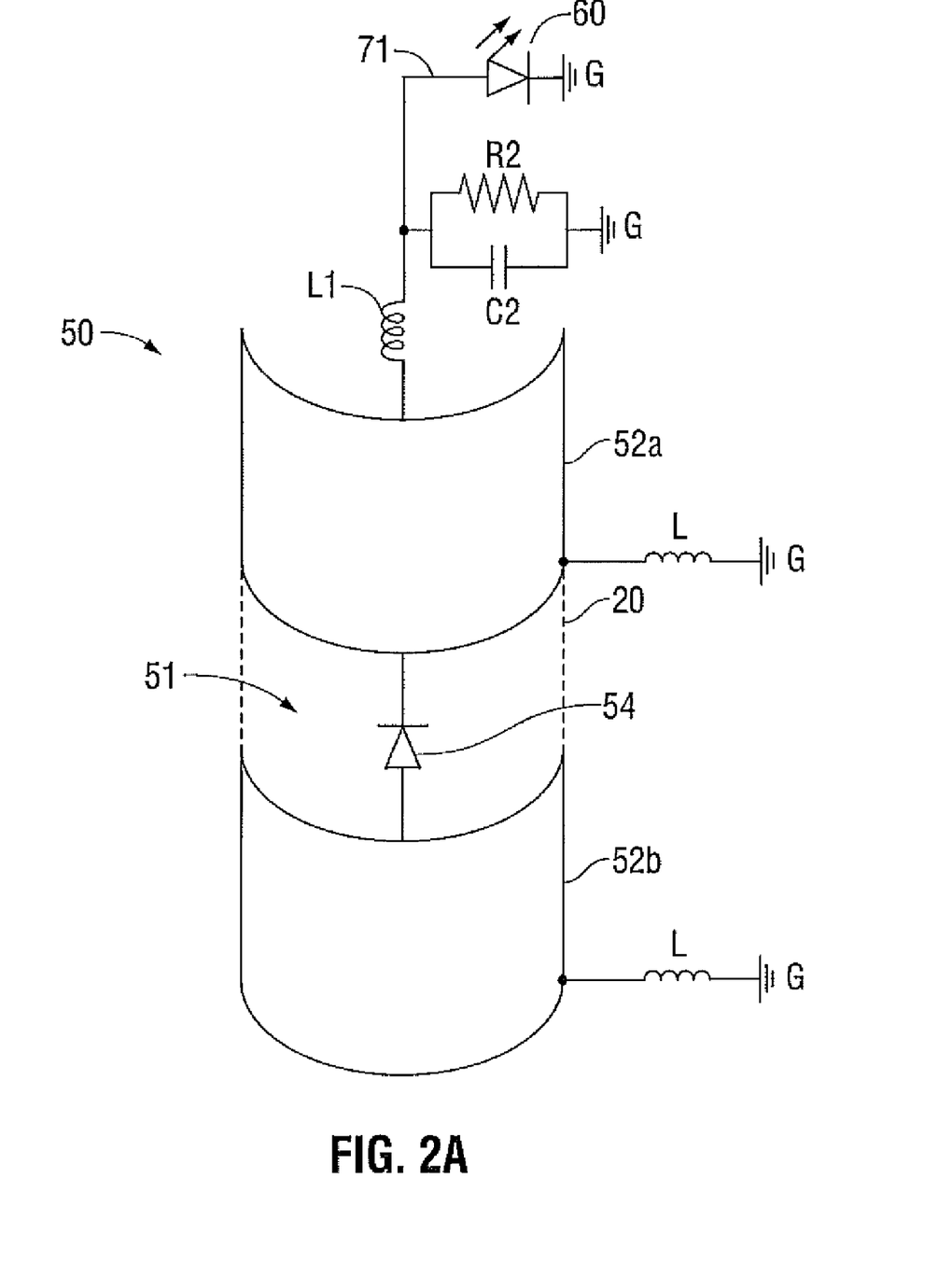
FIGS. 2A-2C are schematic diagrams of a microwave detector according to different embodiments of the present disclosure.

FIG. 2A shows a first embodiment of a radiation detector 50. The radiation detector 50 includes two metal rings 52a-52b that wrap around the feed line 20. The metal rings 52a-52b are connected together using a rectifying device 54 across gap 51. The rectifying device 54 may be any type of suitable diodes such as Zener diode, Schottky diode, tunnel diode and the like. One metal ring 52a is connected LED 60 and ground circuit (R2 and C2 in parallel and G) through inductor L1. Alternatively, both metal rings 52a-52b may be connected to a ground circuit that includes a RF impendence/low DC impedance element L and a ground G. The DC ground connections are made in locations of low RF voltage. The inductor L1 functions as a low pass filter and converts the signal from the rectifying device 54 into a DC signal which is sent across wire 71 to a LED 60, speaker 65, and/or a controller within the generator 14.

The radiation detector 50 may be located anywhere along the feedline 20 and or radiating section 18 as long as the radiation detector 50 is within the patient's abdomen or body cavity. The radiation detector 50 is typically located along the feedline 20 so as to have gap 51 be in a location of high RF voltage.

The metal rings 52a-52b may be formed from a conformal sheet of conductive material such as copper, gold, stainless steel or other conductive metals with similar conductivity values. The width of each ring may be about 0.10 inches to about 2.5 inches with a thickness between about 0.001 inches to about 0.010 inches. The metal rings 52a-52b may be situated over a ground plane with a dielectric insulation providing separation. The dielectric insulation R2 may be formed from a non-conductive conformal material such as polyesters, polyimides, polyamides, polyamide-imides, polyetherimides, polyacrylates, polyethylene terephthalate, polyethylene, polypropylene, polyvinylidene chloride, polysiloxanes, combinations thereof and the like.

Figure 2B:
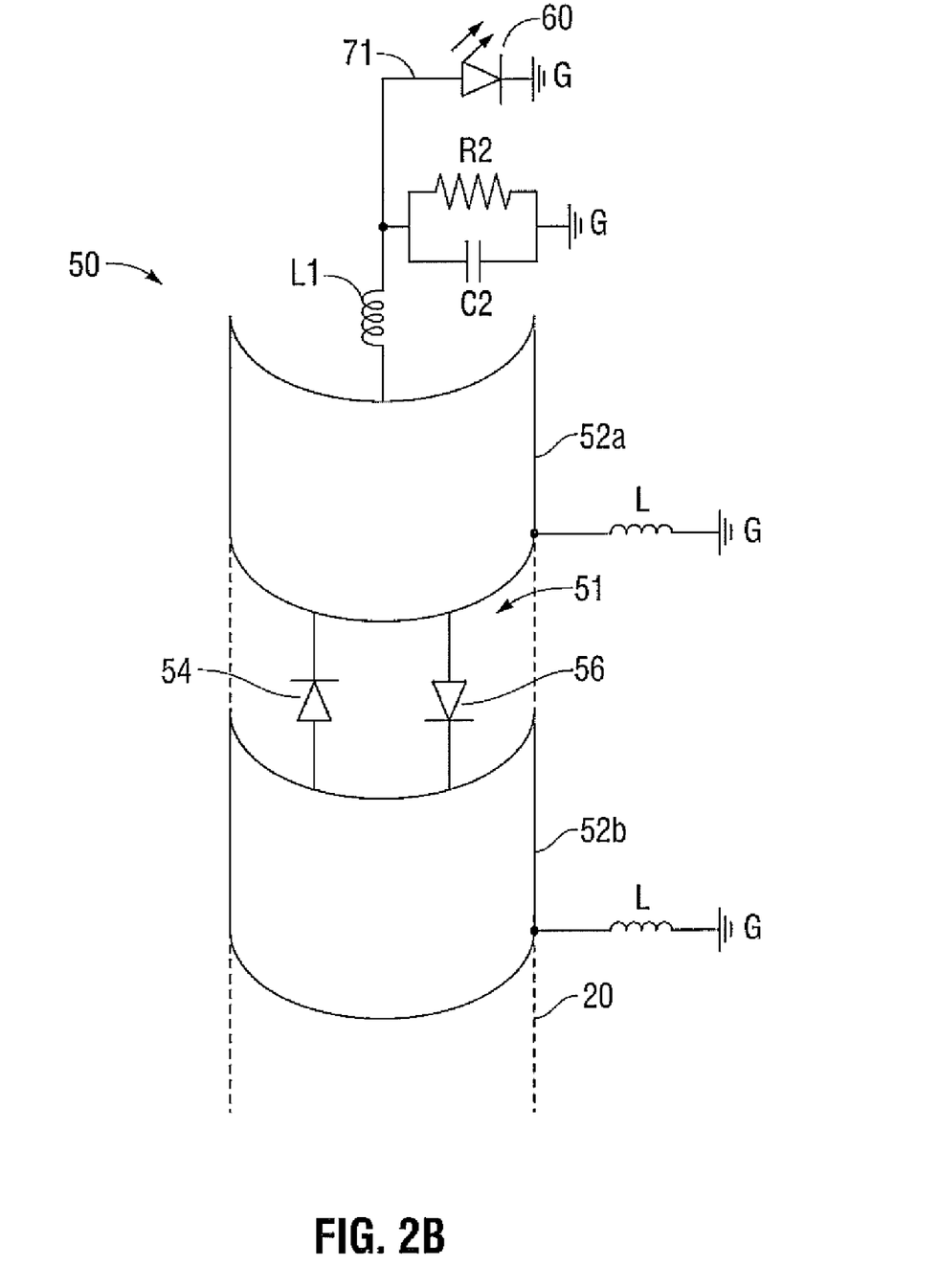

The use of one rectifying device 54 in FIG. 2A allows for half wave rectifying. FIG. 2B shows an alternate embodiment of radiation detector 50 that includes two rectifying devices 54 and 56. The rectifying devices 54 and 56 are soldered to metal pieces 52a-52b in reverse polarity. The rectifying devices 54 and 56 together allow for full wave rectifying.

Figure 2C:
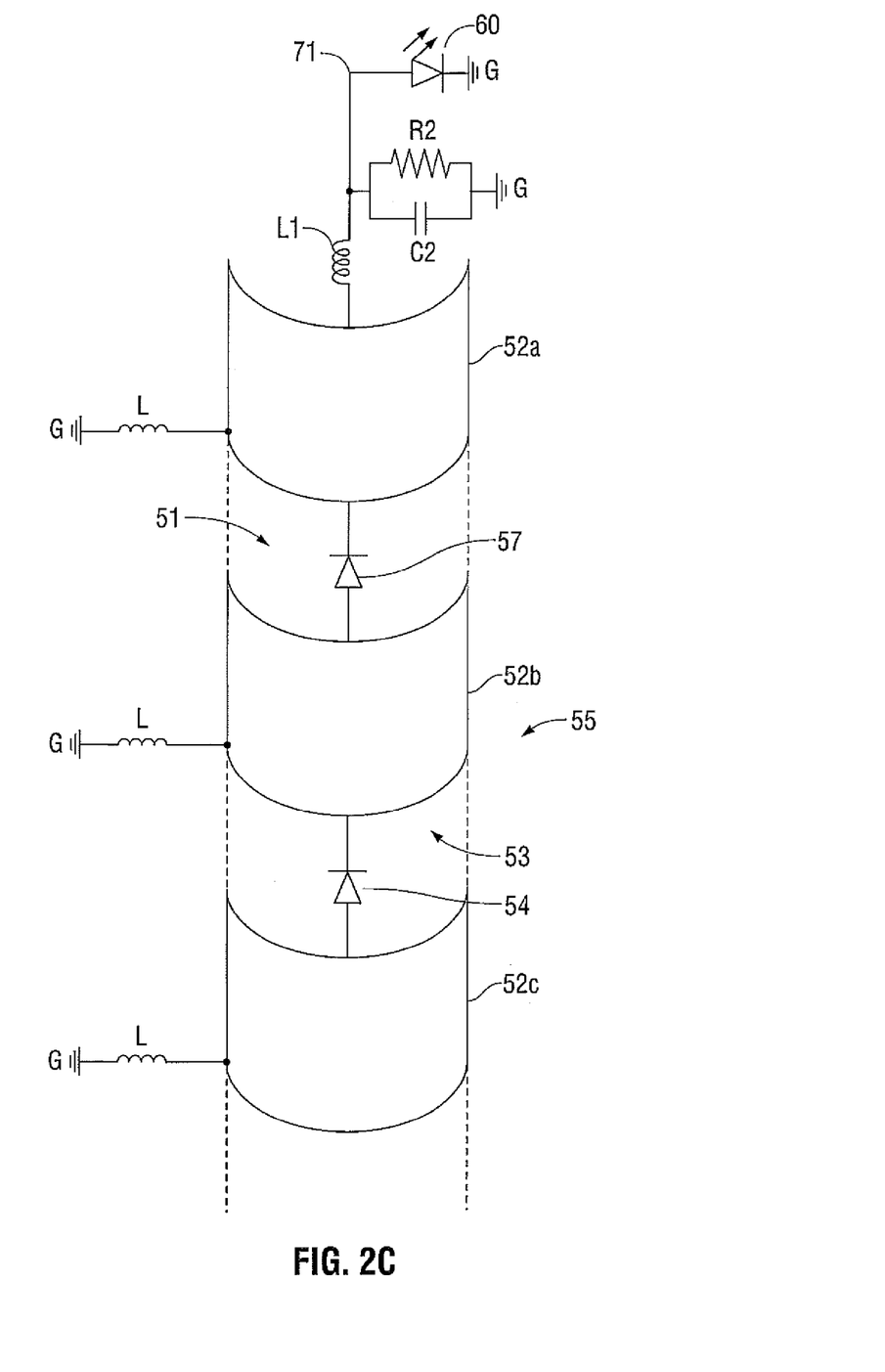

FIG. 2C shows another embodiment of radiation detector 55 that includes three rings 52a-52c. The three rings are connected together with rectifying devices 54 and 57 in the same polarity. The use of three rings allows for a larger antenna aperture and increased bandwidth for detecting rectified microwave energy. Alternatively, the rings 52a-52c may be connected together with the rectifying devices 54 and 57 in reverse polarity. Additionally, two of the rectifying devices (e.g. 54 and 56) may be connected in reverse polarity in each gap 51 and 53, similar to the arrangement shown in FIG. 2B.

Figure 3:
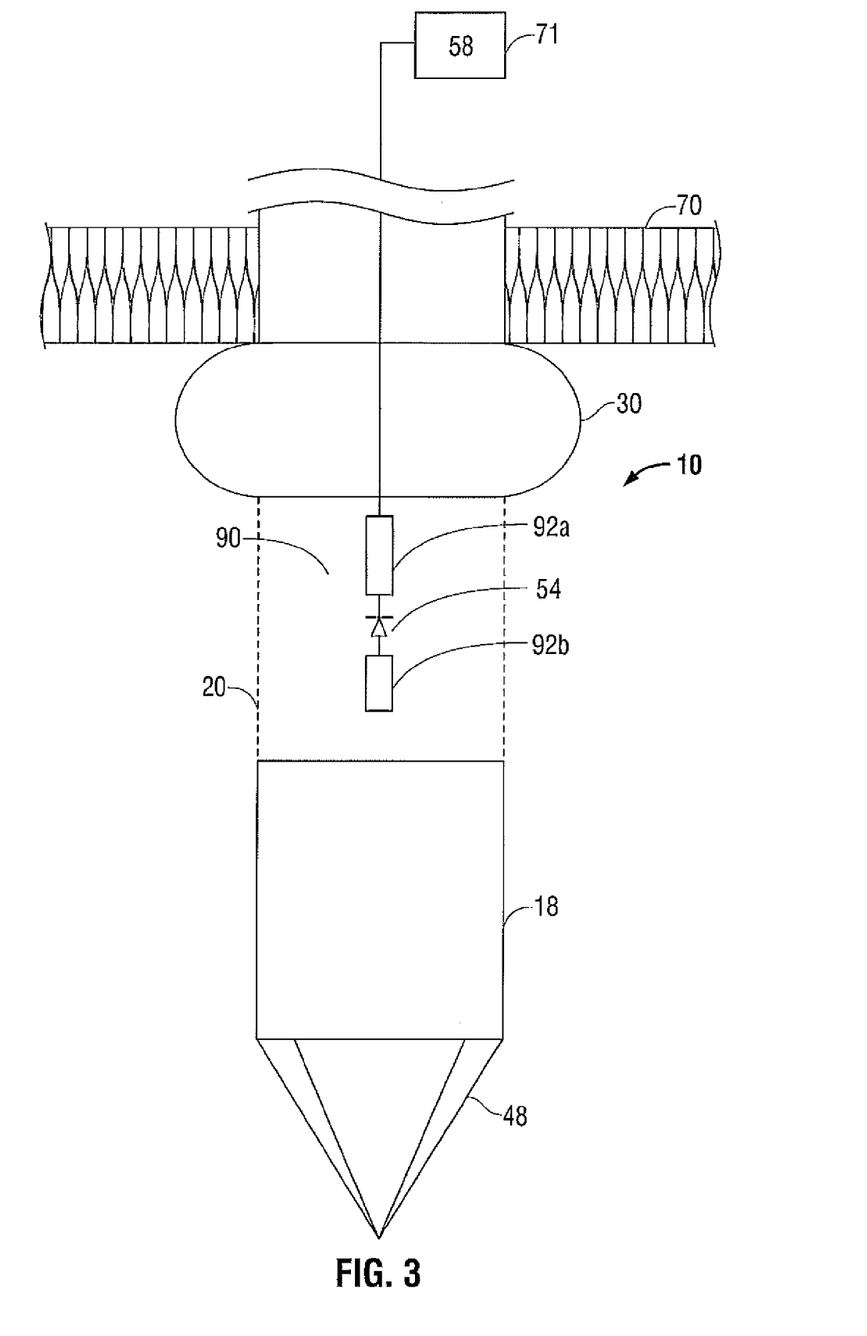
FIG. 3 is a schematic diagram of a linear antenna for use in detecting microwaves according to an embodiment of the present disclosure.

FIG. 3 discloses an alternative radiation detector 90 formed into a linear antenna from two strips of metal 92a-92b. Depending on the operating frequency of the microwave ablation assembly 12, the two strips 92a-92b may have a length and width that range between about 0.1 inches and about 2 inches with a thickness of about 0.005 inches. The strips of metal 92a-92b may be connected together with rectifying device 54. Alternatively, the strips of metal 92a-92b may be connected together with two rectifying devices (e.g. 54 and 56) in reverse polarity to allow for full wave rectification, similar to the arrangement shown in FIG. 2B. The rectifying device 54 is connected to a filter (inductor L1) to convert the signal into a DC signal. The DC signal is sent over wire 71 to a LED 60, speaker 65, and/or a controller in the generator 14. If the DC signal is above a set limit, then the user is notified visually through LED 50, and/or audibly through speaker 65. Alternatively, if the DC signal is above a set limit, then controller may automatically stop sending an electrical signal to the antenna assembly. This limit may vary between about 0.5 volts and about 3 volts based on the operating frequency of the microwave ablation assembly 12. The linear antenna radiation detector 90 may also be used as a patch rectifier or a dipole rectifier.

The strips of metal 92a-92b may be attached to a grounding plane (not shown) with an insulating dielectric between. The strips of metal 92a-92b and grounding plane may be made of conductive material such as copper, gold, stainless steel or other conductive metals with similar conductivity values. The insulating dielectric may be a non-conductive conformal material such as polyesters, polyimides, polyamides, polyamide-imides, polyetherimides, polyacrylates, polyethylene terephthalate, polyethylene, polypropylene, polyvinylidene chloride, polysiloxanes, combinations thereof and the like.

Figure 4:
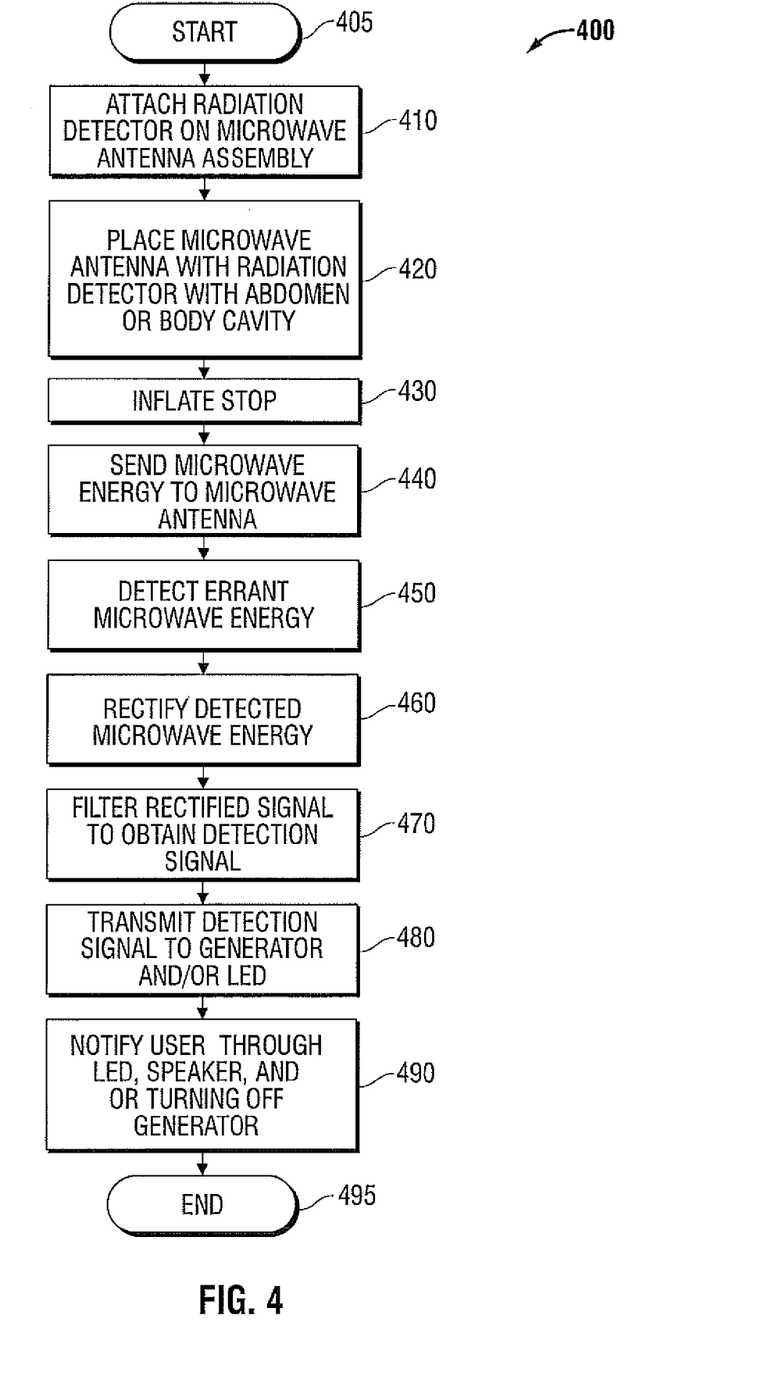
FIG. 4 is a flow chart of a method according to the present disclosure.

FIG. 4 shows a process 400 for detecting errant microwave energy within an insufflated abdomen with reference to radiation detector 50. It should be appreciated that the method may be practiced with other radiation detectors, such as the radiation detector 90, 55 and the like. The process 400 starts at step 405 with an initial step of attaching the radiating detector 50 on the microwave antenna assembly 12 at step 410 which includes wrapping the metal pieces 52a-52b around feedline 20. The method may also include the step of connecting the radiation detector 50 to the generator 14 or another control system. Next, the microwave antenna 12 with radiation detector 50 is placed within a patient's abdomen or body cavity at step 420. Alternatively, the detector 50 may be placed into the insufflated abdomen via a lap port (not shown) and slid over the radiating section 18 and around feedline 20 after insertion of radiating section 18 and feed line 20 through the abdominal wall to reduce gauge size of the device. Detector 50 interfaces with one or more electrode contacts (not shown) on feedline 20. At step 430, the microwave antenna 12 is secured in place within the abdomen. For example, the inflatable stop 30 may be inflated at step 430. Other types of securement materials may also be contemplated. A controller (not shown) in generator 14 may prevent sending electrical energy to the microwave antenna 12 until the microwave antenna 12 is secured, e.g., until the inflatable stop 30 is inflated. Next, at step 440, microwave energy is sent from the generator 14 to microwave antenna 12.

During operation, any errant microwave radiation outside the desired emission area, such as outside the radiating section 18, is picked up by the radiation antenna 50, namely, the metal rings 52a-52h at step 450. The detected microwave energy is then rectified by rectifier 54 at step 460 and the rectified signal is filtered by a filter into a detection signal (e.g., a DC voltage signal 71) at step 470. The filter may include a simple inductor L1, or inductor resistor series elements (not shown). The detection signal is then transmitted to generator 14, LED 60, and/or speaker 65 at step 480. The generator 14 and/or other control circuitry (not shown) compares the detection signal to a threshold value to determine whether the level of the microwave energy is unsafe. If the determination is made that the level of microwave energy is excessive, the generator 14 may either suspend the supply of microwave energy and/or notify the user of this occurrence at step 490 prior to process 400 ending at step 495. The user may be notified using speaker 65 and/or LED 60.

The described embodiments of the present disclosure are intended to be illustrative rather than restrictive, and are not intended to represent every embodiment of the present disclosure. Various modifications and variations can be made without departing from the spirit or scope of the disclosure as set forth in the following claims both literally and in equivalents recognized in law.

What is claimed is:

1. A radiation detector disposed on a microwave antenna assembly, the radiation detector, comprising:
   a receiving antenna adapted to receive microwave energy, wherein the receiving antenna is formed from two pieces of metal externally attached to a microwave antenna of the microwave antenna assembly;
   at least one rectifier coupled between the pieces of metal adapted to rectify at least a portion of the microwave energy; and
   a filter coupled to the at least one rectifier and adapted to convert the rectified microwave energy into a detection signal.

2. The radiation detector according to claim 1, wherein the receiving antenna further comprises:
   two dielectric substrates each having a top surface and a bottom surface;
   each piece of metal is disposed on the top surface of each dielectric substrate; and
   a grounding member disposed on the bottom surface of each dielectric substrate, wherein the antenna and grounding members are electrically insulated by the dielectric substrate.

3. The radiation detector according to claim 2, wherein the dielectric substrate is formed from a non-conductive, conformal material and the grounding member are formed from a conductive, conformal material.

4. The radiation detector according to claim 1, wherein the at least one rectifier is a diode.

5. The radiation detector according to claim 1, further comprising:
   a light-emitting device coupled to the filter, the light-emitting device adapted to operate when the detection signal is above a predetermined threshold signal.

6. The radiation detector according to claim 1, wherein the two pieces of metal have a geometry of a ring, a patch, a linear strip, or a combination of geometries.

7. The radiation detector according to claim 1, further comprising:
   a speaker coupled to the filter, the speaker adapted to operate when the detection signal is above a predetermined threshold signal.

8. The radiation detector according to claim 1, wherein the receiving antenna further comprises:

a third piece of metal externally attached to the antenna of the microwave antenna assembly, wherein the third piece of metal is coupled to the two pieces of metal with a second rectifier.

9. The radiation detector according to claim 1, wherein the radiation detector is located on the distal end of the microwave antenna within an abdomen of a patient.

10. The radiation detector according to claim 1, further comprising a gap between the two metal pieces and the gap is located along the antenna at a position of a high RF voltage.

11. The radiation detector according to claim 1, further comprising a second rectifier coupled between the two metal pieces, wherein the two rectifiers are soldered to the metal pieces in reverse polarities.

12. A microwave antenna assembly, comprising:
a hub adapted to couple the microwave antenna assembly to a microwave generator;
a radiating section coupled to the hub through a feedline;
an inflatable stop surrounding the feedline, wherein the inflatable stop is inflated when the feedline is placed within an abdomen of a patient to prevent the radiating section from inadvertently withdrawing from the abdomen; and
a radiation detector disposed on the microwave antenna assembly near the radiating section, the radiation detector comprising:
a receiving antenna adapted to receive microwave energy, wherein the receiving antenna is formed from two pieces of metal externally attached to the feedline within the abdomen;
at least one rectifier coupled between the pieces of metal adapted to rectify at least a portion of the microwave energy that resonates in the abdomen; and
a filter coupled to the at least one rectifier and adapted to convert the rectified microwave energy into a detection signal.

13. The microwave antenna assembly according to claim 12, wherein the receiving antenna is a ring antenna, and the receiving antenna further comprises:
two dielectric substrates each having a top surface and a bottom surface;
each piece of metal is disposed on the top surface of each dielectric substrate; and
a grounding member disposed on the bottom surface of each dielectric substrate, wherein the antenna and grounding members are electrically insulated by the dielectric substrate.

14. The microwave antenna assembly according to claim 12, wherein the feedline includes an outer conductor and the receiving antenna is a linear antenna disposed on the outer conductor of the feedline such that a longitudinal axis of the linear antenna is substantially parallel to a longitudinal axis of the feedline.

15. The microwave antenna assembly according to claim 12, wherein the receiving antenna further comprises a gap between the two metal pieces and the gap is located along the feedline at a position of a high RF voltage.

16. The microwave antenna assembly according to claim 12, wherein the receiving antenna is located near a distal end of the inflatable stop.

17. A method for detecting microwave energy, the method comprising:
receiving resonant microwave energy from an insulfated abdomen with a receiving antenna;
rectifying at least a portion of the microwave energy through at least one rectifier coupled to the receiving antenna; and
filtering the rectified microwave energy through a filter coupled to the at least one rectifier to convert the rectified microwave energy into a detection signal.

18. The method according to claim 17, further comprising:
comparing the detection signal with a predetermined threshold signal; and
suspending supply of microwave energy based on the comparison of the detection signal with the predetermined threshold signal.

19. The method according to claim 17, further comprising:
comparing the detection signal with a predetermined threshold signal; and
providing an alert based on the comparison of the detection signal with the predetermined threshold signal, wherein the alert is a visual or audible alert.

20. The method according to claim 17, further comprising:
inserting a radiating section of a microwave antenna assembly within an abdomen of a patient; and
inflating an inflatable stop to ensure the radiating section is positioned within the abdomen and preventing the radiating section from unintentionally withdrawing from the abdomen.

* * * * *